(12) United States Patent  
Grady et al.

(10) Patent No.: US 10,304,569 B2  
(45) Date of Patent: May 28, 2019

(54) SYSTEMS AND METHODS FOR ASSOCIATING MEDICAL IMAGES WITH A PATIENT

(71) Applicant: HeartFlow, Inc., Redwood City, CA (US)

(72) Inventors: Leo Grady, Millbrae, CA (US); Christopher Zarins, Menlo Park, CA (US); Edward Karl Hahn, III, San Carlos, CA (US); Ying Bai, Belmont, CA (US); Sethuraman Sankaran, Palo Alto, CA (US); Peter Kersten Petersen, Palo Alto, CA (US); Michiel Schaap, Redwood City, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/367,885

(22) Filed: Dec. 2, 2016

(65) Prior Publication Data

US 2017/0161455 A1 Jun. 8, 2017

Related U.S. Application Data

(60) Provisional application No. 62/262,553, filed on Dec. 3, 2015.

(51) Int. Cl.
*G06F 19/00* (2018.01)
*A61B 5/00* (2006.01)
(Continued)

(52) U.S. Cl.
CPC ........... *G16H 50/50* (2018.01); *A61B 5/4842* (2013.01); *A61B 5/4848* (2013.01);
(Continued)

(58) Field of Classification Search
CPC ... G06F 19/343; A61B 5/4842; A61B 5/4848; A61B 5/742; A61B 5/7271; A61B 2576/00
See application file for complete search history.

(56) References Cited

U.S. PATENT DOCUMENTS 9,530,203 B2 * 12/2016 Kimoto .................. A61B 6/032
9,839,483 B2 * 12/2017 Sankaran ............... G16H 30/40
(Continued)

FOREIGN PATENT DOCUMENTS

EP          0 867 830         9/1998

OTHER PUBLICATIONS

International Search Report and the Written Opinion issued in related PCT/US16/064741 dated Mar. 9, 2017 (11 pages).

*Primary Examiner* — Bobbak Safaipour
(74) *Attorney, Agent, or Firm* — Bookoff McAndrews, PLLC (57) ABSTRACT

Systems and methods are disclosed for associating medical images with a patient. One method includes: receiving two or more medical images of patient anatomy in an electronic storage medium; generating an anatomical model for each of the received medical images; comparing the generated anatomical models; determining a score assessing the likelihood that the two or more medical images belong to the same patient, using the comparison of the generated anatomical models; and outputting the score to an electronic storage medium or display.

20 Claims, 7 Drawing Sheets

(51) Int. Cl.
*G16H 50/50* (2018.01)
*G06T 7/00* (2017.01)
*G16H 10/60* (2018.01)

(52) U.S. Cl.
CPC ............ *A61B 5/7271* (2013.01); *A61B 5/742* (2013.01); *G06F 19/00* (2013.01); *G06F 19/321* (2013.01); *G06T 7/0016* (2013.01); *G16H 10/60* (2018.01); *A61B 2576/00* (2013.01)

(56) References Cited

U.S. PATENT DOCUMENTS

| | | | |
|---|---|---|---|
| 2004/0101180 A1 | 5/2004 | Doi | |
| 2009/0262894 A1* | 10/2009 | Shukla | A61N 5/1049 378/65 |
| 2010/0098309 A1* | 4/2010 | Graessner | G06K 9/00 382/131 |
| 2011/0238444 A1 | 9/2011 | Klingler | |
| 2012/0041323 A1* | 2/2012 | Taylor | A61B 5/02007 600/508 |
| 2013/0223702 A1* | 8/2013 | Holsing | A61B 5/113 382/128 |
| 2013/0251099 A1* | 9/2013 | Kunz | A61B 5/117 378/19 |
| 2014/0031668 A1* | 1/2014 | Mobasser | A61B 5/062 600/409 |
| 2015/0073765 A1* | 3/2015 | Boettger | A61B 5/7275 703/11 |
| 2015/0302578 A1* | 10/2015 | Grady | G06T 7/0012 382/131 |
| 2015/0348260 A1* | 12/2015 | Sharma | G06T 7/0012 600/480 |
| 2015/0374243 A1* | 12/2015 | Itu | G16H 50/50 703/2 |
| 2016/0066930 A1* | 3/2016 | Geebelen | A61B 17/155 606/88 |
| 2016/0135738 A1* | 5/2016 | Bowers | A61B 5/4833 600/301 |
| 2016/0220124 A1* | 8/2016 | Grady | A61B 5/026 |
| 2016/0247312 A1* | 8/2016 | Santhanam | G06T 15/08 |
| 2016/0314601 A1* | 10/2016 | Sankaran | G16H 50/50 |
| 2016/0367264 A1* | 12/2016 | Geebelen | A61B 17/155 |
| 2017/0132388 A1* | 5/2017 | Grady | G16H 50/50 |
| 2017/0367580 A1* | 12/2017 | DiMaio | A61B 5/0064 |

* cited by examiner

SYSTEMS AND METHODS FOR ASSOCIATING MEDICAL IMAGES WITH A PATIENT

RELATED APPLICATION(S)

This application claims priority to U.S. Provisional Application No. 62/262,553, filed Dec. 3, 2015, the entire disclosure of which is hereby incorporated herein by reference.

FIELD OF THE DISCLOSURE

Various embodiments of the present disclosure relate generally to medical imaging, image association and/or matching, and related methods. More specifically, particular embodiments of the present disclosure relate to systems and methods for associating one or more medical images to a patient.

BACKGROUND

In order to study the progression or regression of disease in a patient or determine the effectiveness of a treatment, it may be useful to associate medical images obtained at different time points with the same individual patient. Although patient biographical data (e.g., patient name, date of birth, medical history, patient gender, weight, height, body mass index, hair color, or eye color) may be available to assist with this association, typographic errors in data entry may result in the same patient having different patient biographical data (e.g., two slightly different names or birthdates) in a medical record. Additionally, some patients may share the same patient biographical data. For example, some patients with common names may share the same birthdate. Further, as patients move to different hospitals, patient biographical data may be stored differently across hospitals or may be unavailable at one or more locations.

Biometric methods may exist for matching 2D infrared images of vein patterns in the palm or finger to establish a person's identity. However, these methods may not address the complexities that arise when matching medical images to a patient, in the context of diagnosis or treatment, for several reasons. Unlike the images of the veins of a palm or finger obtained for security purposes, medical images of a patient may be affected by substantial changes due to age, disease progression or regression, treatment, medical intervention (e.g., placement of a stent, bypass, resection, ablation, embolization, amputation, etc.), trauma, and/or care. Unlike image acquisition of a patient in the context of medical diagnosis or treatment, an image acquisition of the vein pattern of a palm or finger in the context of security may be controlled, such that the same field of view is captured, and the imaging equipment may be standardized to use the same device for all images. In contrast, there may be differences in medical image acquisition protocol (e.g., reconstruction kernels, patient preparation protocol, patient physiological state at the time of imaging, imaging field of view, etc.), medical imaging device (e.g., spatial or temporal resolution, scanner vendor or model, etc.) and/or medical imaging modality (e.g., computerized tomography (CT), magnetic resonance (MR), positron emission tomography (PET), single-photon emission computed tomography (SPECT), angiography, etc.), when matching medical images to a patient. Unlike images of a vein pattern in a palm or finger obtained for security purposes, medical images of a patient may change as a result of a patient's preparation or physiological state. Foreign bodies (e.g., implanted medical devices) may be unlikely to be present in the images of a palm or finger, unlike medical images of a patient's anatomy. Unlike infrared imaging, which is used for matching vein patterns, medical imaging equipment used for patients may be prone to the imaging artifacts (e.g., metal artifacts in CT).

Therefore, a need exists for an automated system and method of linking medical images of the same patient, even in the presence of typographic errors, duplicate patient biographical data (e.g., names, birthdates, etc.), multiple medical institutions, and/or various platforms for electronic medical records, and which may overcome the limitations of biometric methods matching 2D infrared images of vein patterns. Furthermore, a need exists for a system and method of matching medical images that may be augmented by using patient biographical data (e.g., patient name, date of birth, gender, weight, height, body mass index, hair color, eye color, etc.) to enhance the opportunity to provide a reliable association of multiple images to a patient.

The foregoing general description and the following detailed description are exemplary and explanatory only and are not restrictive of the disclosure.

SUMMARY

According to certain aspects of the present disclosure, systems and methods are disclosed for associating one or more medical images with a patient.

One method includes: receiving two or more medical images of patient anatomy in an electronic storage medium; generating an anatomical model for each of the received medical images; comparing the generated anatomical models; determining a score assessing the likelihood that the two or more medical images belong to the same patient, using the comparison of the generated anatomical models; and outputting the score to an electronic storage medium or display.

In accordance with another embodiment, a system associating medical images with a patient comprises: a data storage device storing instructions for associating medical images with a patient; and a processor configured for: receiving two or more medical images of patient anatomy in an electronic storage medium; generating an anatomical model for each of the received medical images; comparing the generated anatomical models; determining a score assessing the likelihood that the two or more medical images belong to the same patient, using the comparison of the generated anatomical models; and outputting the score to an electronic storage medium or display.

In accordance with another embodiment, a non-transitory computer readable medium for use on a computer system containing computer-executable programming instructions for performing a method of associating medical images with a patient, the method comprising: receiving two or more medical images of patient anatomy in an electronic storage medium; generating an anatomical model for each of the received medical images; comparing the generated anatomical models; determining a score assessing the likelihood that the two or more medical images belong to the same patient, using the comparison of the generated anatomical models; and outputting the score to an electronic storage medium or display.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts or steps of a method.

Associating medical images obtained at different time points for an individual patient may enhance the study of progression or regression of disease in the patient or determine the effectiveness of a treatment. Although patient biographical data (e.g., patient name and birthdate) may be available to assist with this association, typographic errors in data entry may result in the same patient having different patient biographical data (e.g., two slightly different names or birthdates) in a medical record. Additionally, some patients may share the same patient biographical data.

Further, as patients move to different hospitals, patient biographical data may be stored differently across hospitals and various electronic medical record platforms, or may be unavailable at one or more locations. In addition, patient medical images may be transferred between medical facilities, e.g., for various forms of processing, analysis, and/or storage. Various medical facilities may be subject to different regulations as to what types of patient biographical data may be stored or transferred with the patient medical images. For instance, some regulations may cause patient medical images to be disassociated from one or more forms of patient biographical data (e.g., name or date of birth) if and when the patient medical images are transferred to/between processing, analytical, and/or storage entities.

There may be complexities that arise when matching medical images to a patient, in the context of diagnosis or treatment, for several reasons. Medical images of a patient may be affected by substantial changes due to age, disease progression or regression, treatment, medical intervention (e.g., implantation of a stent or other device, bypass, resection, ablation, embolization, amputation, etc.), trauma, and/or care. Image acquisition of a patient, in the context of medical diagnosis or treatment, may not typically be controlled, such that the same field of view may not always be captured, and the imaging equipment may be not be standardized to use the same device for all images. In addition, there may be differences in medical image acquisition protocol (e.g., reconstruction kernels, patient preparation protocol, patient physiological state at the time of imaging, imaging field of view, etc.), medical imaging device (e.g., spatial or temporal resolution, scanner vendor or model, etc.) and/or medical imaging modality (e.g., CT, MR, PET, SPECT, angiography, etc.), when matching medical images to a patient. Additionally, medical images of a patient may change as a result of a patient's preparation or physiological state, may reveal the presence of foreign bodies (e.g., implanted medical devices), and may be prone to the imaging artifacts (e.g., metal artifacts in CT).

Therefore, an automated system and method of linking medical images of the same patient, even in the presence of typographic errors, duplicate patient biographical data (e.g., names, birthdays, etc.), and/or across multiple medical institutions, and which may overcome the limitations of biometric methods matching 2D infrared images of vein patterns, may be useful. The systems and methods of the present disclosure for associating medical images with a patient addresses and overcomes the above issues and may allow for new biometric patterns and additional information to be used to complete the association. Additionally, the systems and methods of the present disclosure may access patient biographical data (e.g., names, birthdates, etc.), which is atypical for biometric methods that match vein patterns in a palm or finger in a security context. Having patient biographical data may further enhance the opportunity to provide a reliable association between patients, e.g., patients that are biologically related to each other.

Figure 1:
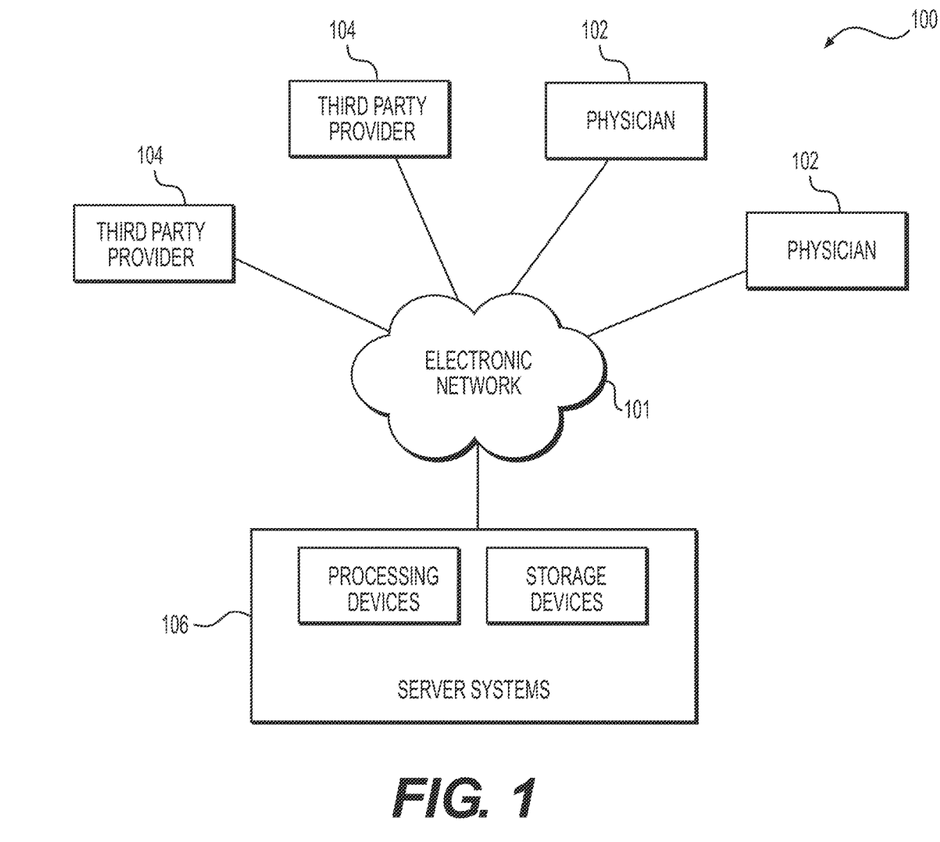
FIG. 1 is a block diagram of an exemplary system and network for associating one or more medical images with a patient, according to an exemplary embodiment of the present disclosure.

Referring now to the figures, FIG. 1 depicts a block diagram of an exemplary system 100 and network for associating medical images with a patient, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific biographical information, including, but not limited to, patient age, date of birth, medical history, and information regarding patient gender weight, height, body mass index, hair color, or eye color.

Physicians 102 and/or third party providers 104 may transmit the anatomical images and/or patient-specific biographical information to server systems 106 over the electronic network 101. Server systems 106 may include storage devices for storing images and data received from physicians 102 and/or third party providers 104. Server systems 106 may also include processing devices for processing images and data stored in the storage devices.

Figure 2:
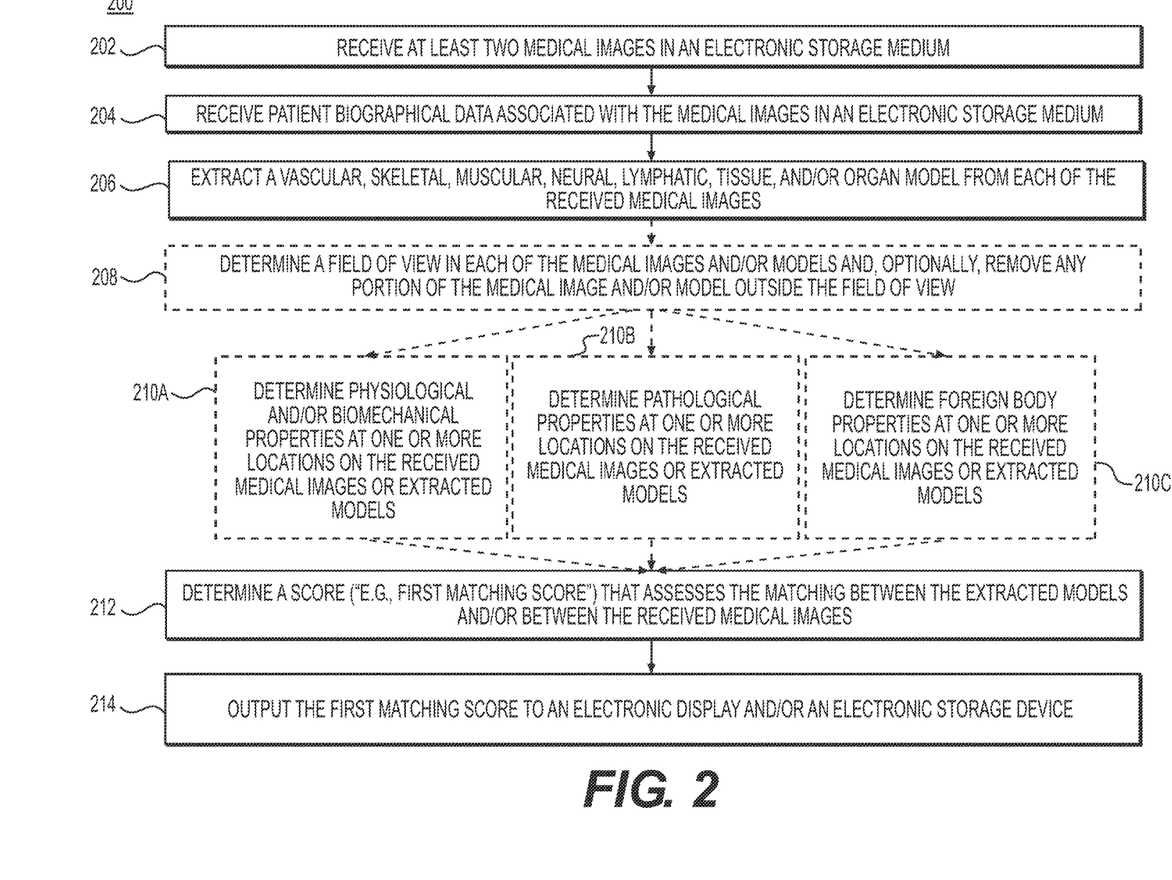
FIG. 2 is a block diagram of an exemplary method of associating medical images with a patient, according to an embodiment of the present disclosure.
Figure 3:
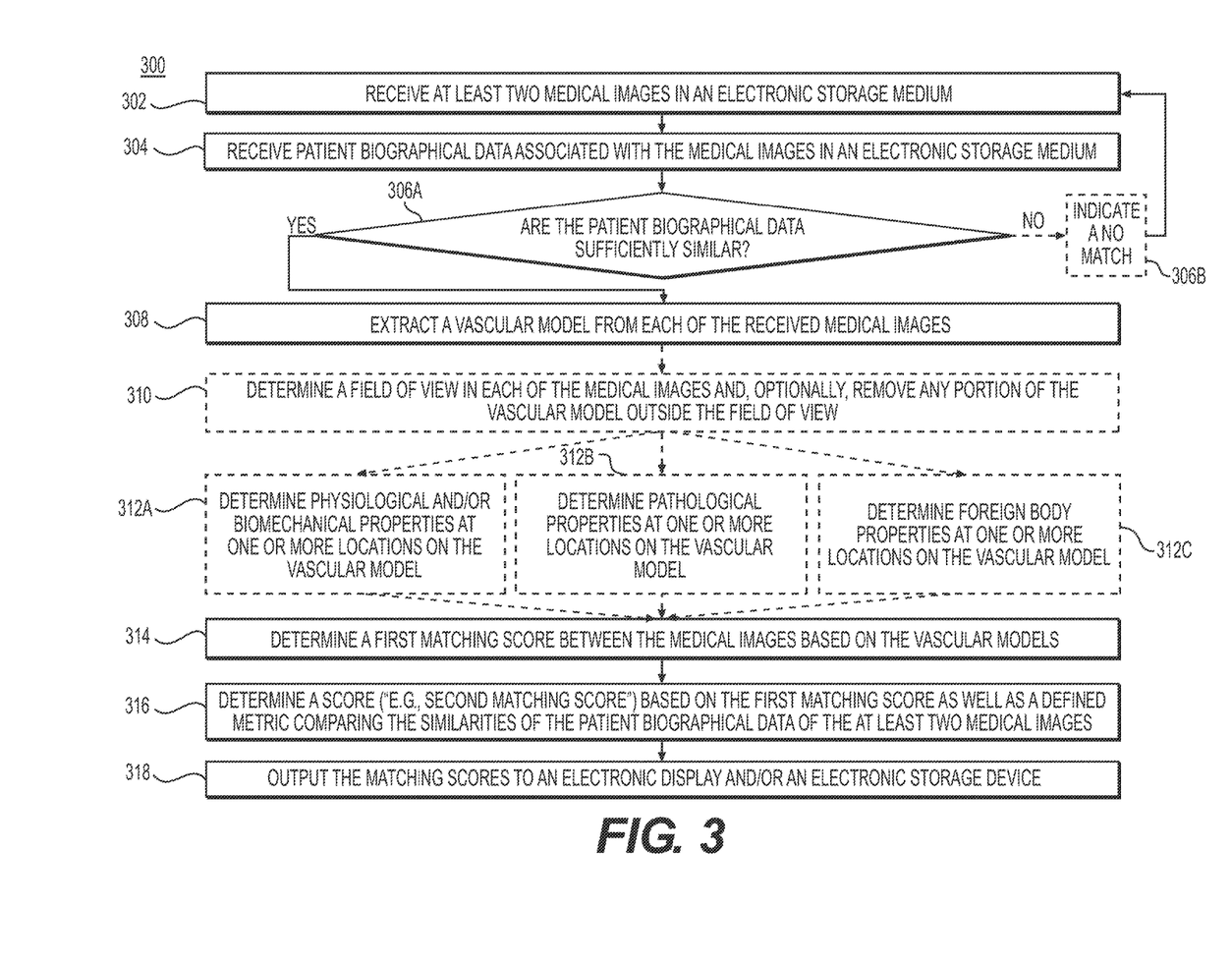
FIG. 3 is a block diagram of another exemplary method of associating one or more medical images with a patient, by extracting a vascular model from each of the received medical images and further adjusting a matching score based on the received patient biographical information, according to a further embodiment of the present disclosure.
Figure 4:
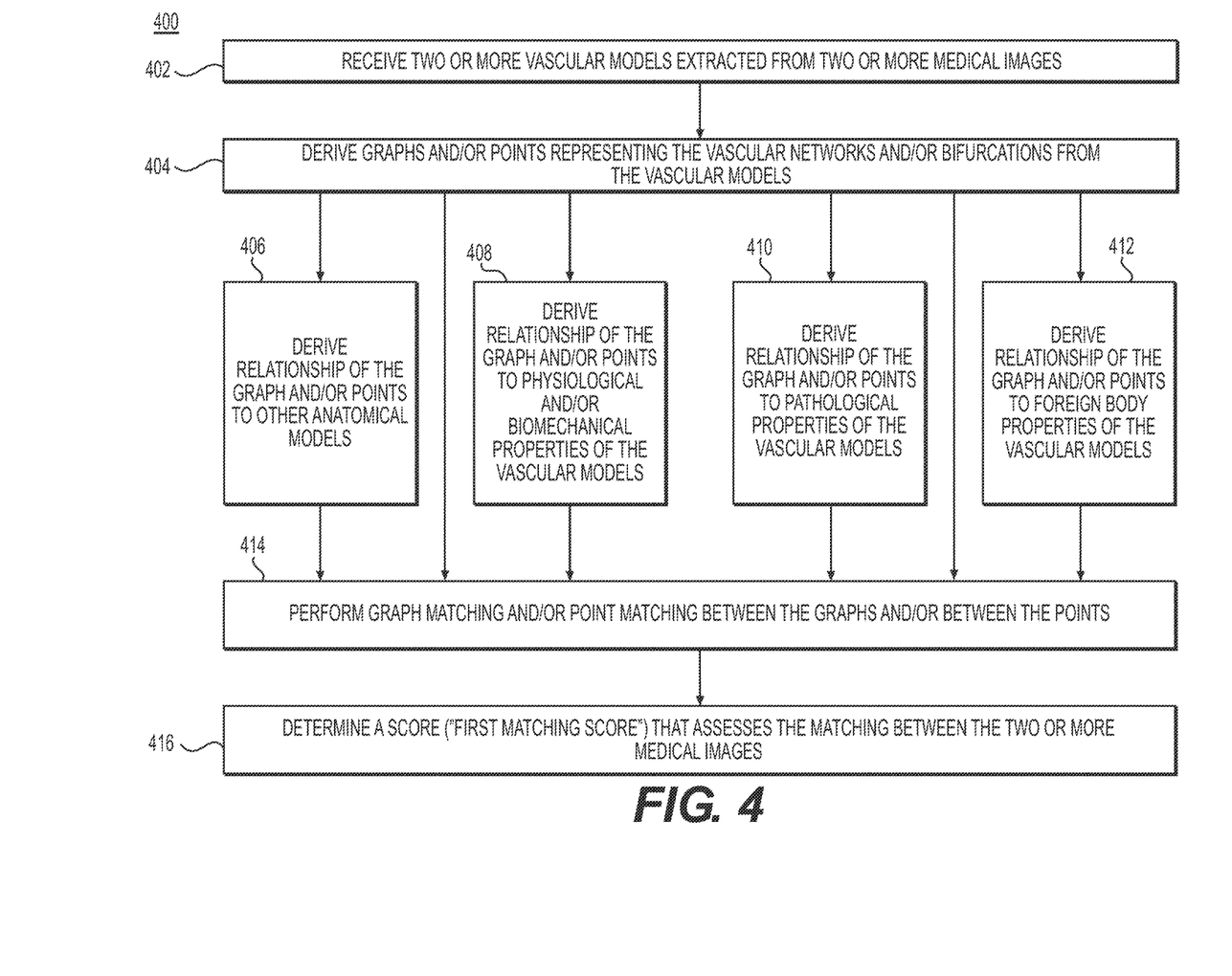
FIG. 4 is a block diagram of yet another exemplary method of determining a first matching score between two or more medical images by using graph or point matching, according to an embodiment of the present disclosure.
Figure 5:
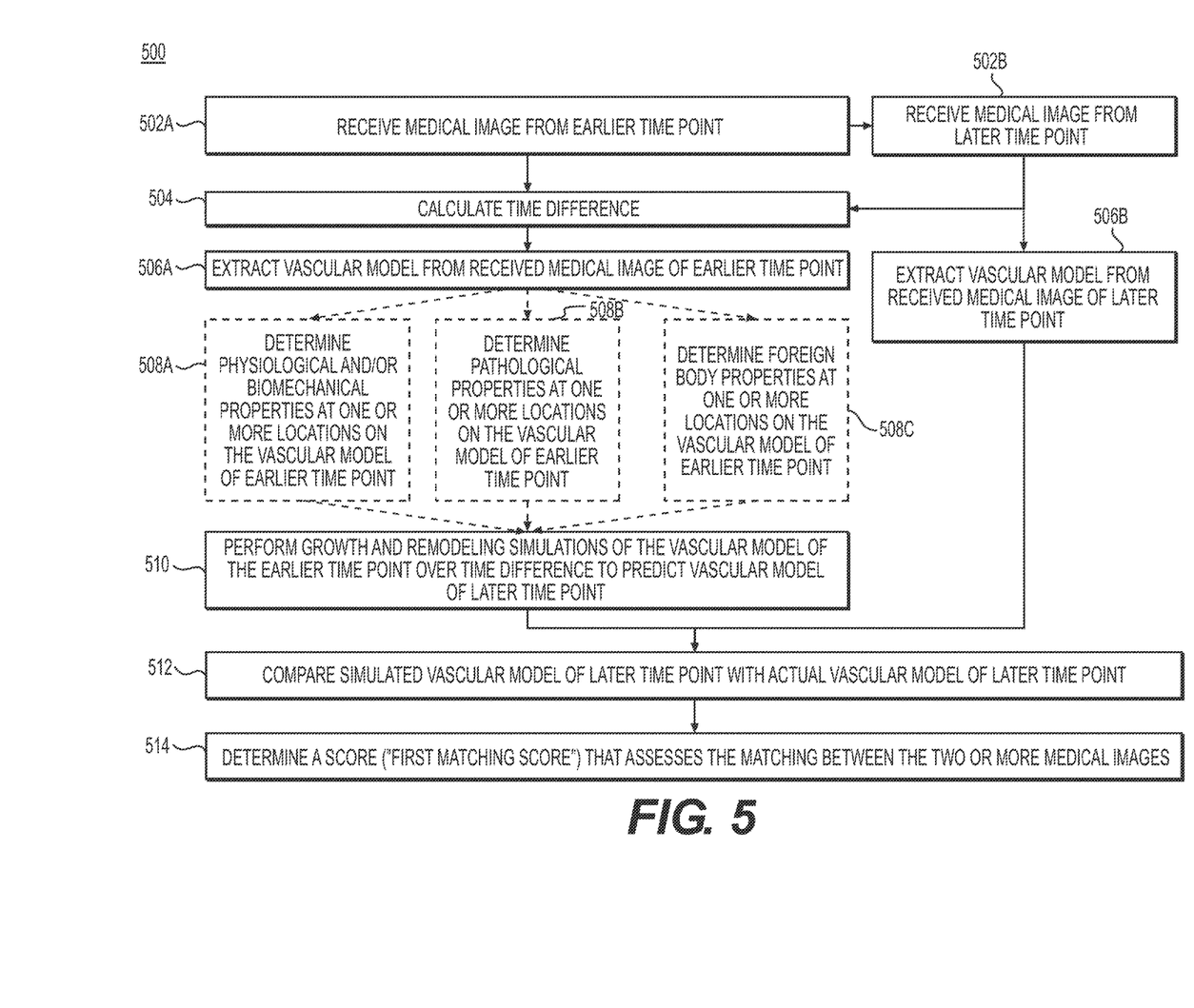
FIG. 5 is a block diagram of another exemplary method of determining a first matching score between two or more medical images by using growth and remodeling simulations, according to another embodiment.
Figure 6:
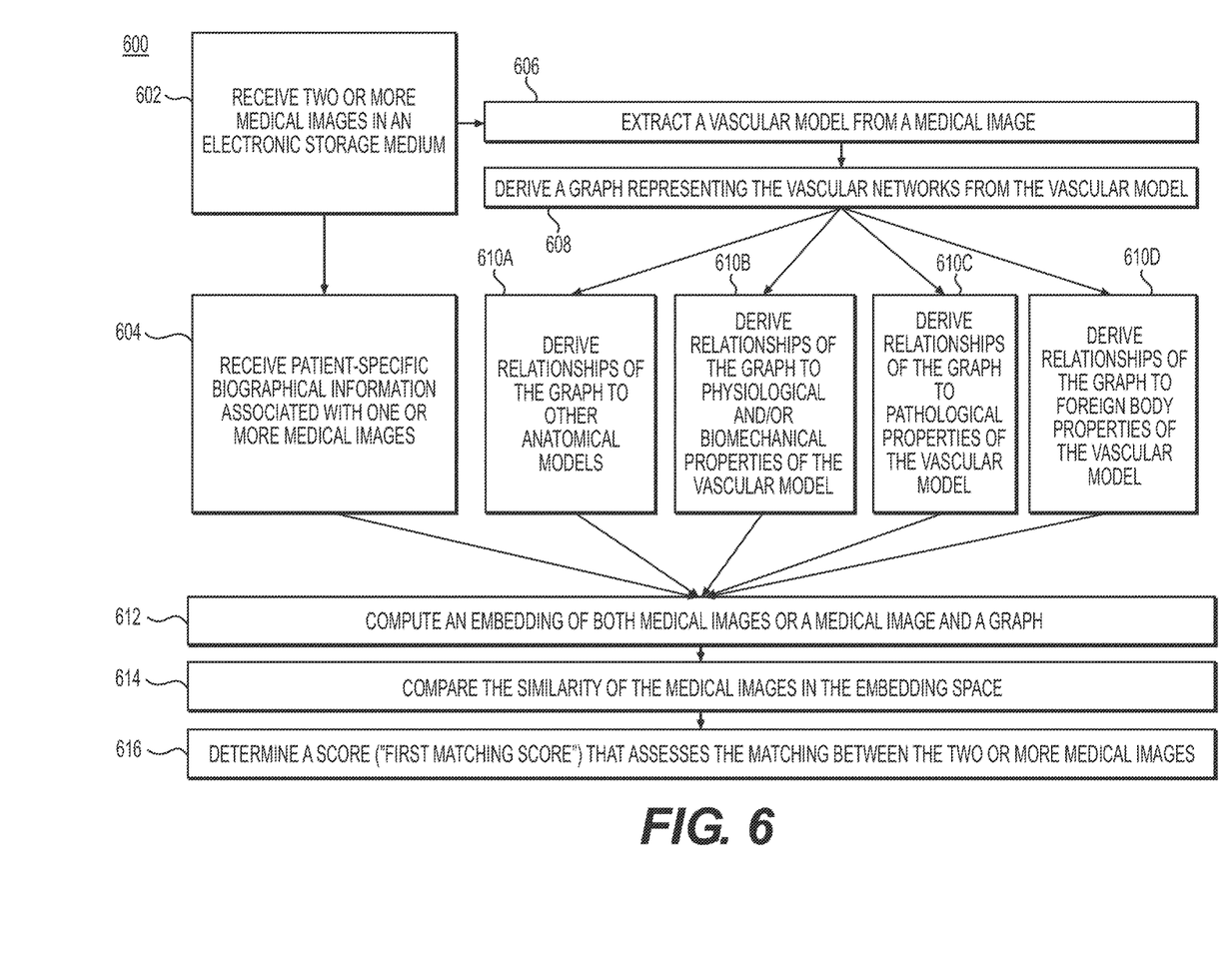
FIG. 6 is a block diagram of an exemplary method for determining a first matching score between two or more medical images by computing an embedding of the two or more medical images or a medical image and a graph.
Figure 7:
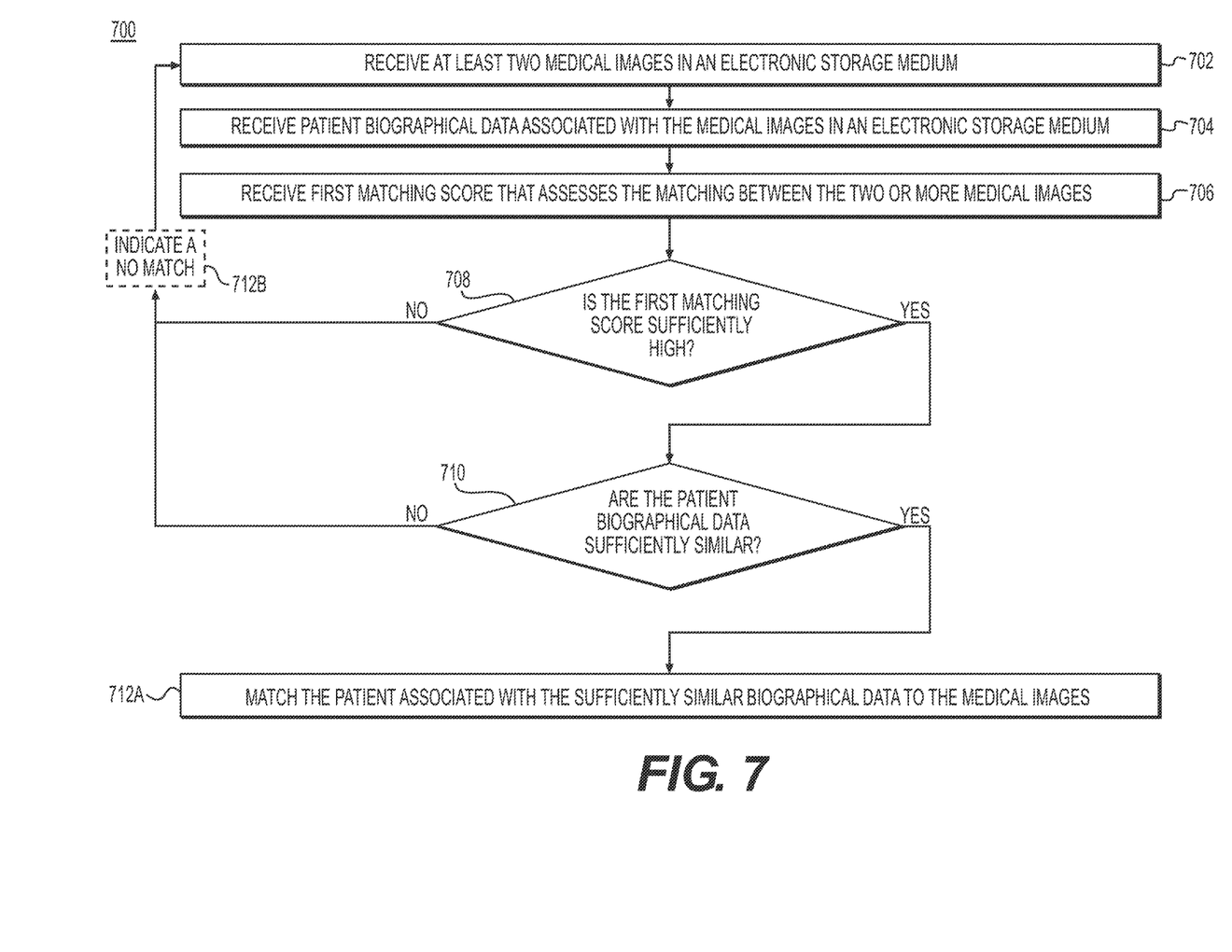
FIG. 7 is a block diagram of another exemplary method for associating at least two medical images with a patient using a first matching score and patient biographical data.

FIG. 2 depicts a first exemplary embodiment of a method for associating medical images with a patient. FIG. 3 depicts another exemplary embodiment of the method of FIG. 2 where the process of associating medical images with a patient includes, among other things, extracting a vascular model from each of the received medical images and further adjusting the matching score based on the received patient biographical information. FIGS. 4, 5, and 6 depict various methods for, among other things, comparing medical images and/or vascular models extracted from medical images for the purpose of determining a score (e.g., a "first matching score") that assesses the matching between the received medical images and/or extracted vascular models. FIG. 7 depicts an exemplary embodiment of a method of associating medical images to an identifiable patient using the computed first matching score and the received patient biographical data.

FIG. 2 is a block diagram of a method 200 of associating medical images with a patient, according to a general embodiment. The method of FIG. 2 may be performed by server systems 106, based on information, images, and data received from physicians 102 and/or third party providers 104 over electronic network 101.

In one embodiment, step 202 may include receiving two or more medical images of a patient anatomy in an electronic storage medium of the server systems 106. Specifically, receiving the patient-specific medical images may include either generating the patient-specific medical images at the server system 106, and/or receiving them over an electronic network (e.g., electronic network 101). In one embodiment, the medical images may be derived from images of one or more patients acquired via one or more available imaging or scanning modalities (e.g., computed tomography (CT), magnetic resonance imaging (MRI), single-photon emission computed tomography (SPECT), positron emission tomography (PET), ultrasound imaging, multi-view angiography, etc.). For example, the images may be received from a plurality of facilities. Alternatively or in addition, the medical images may be generated or acquired at different times. For instance, one medical image may be acquired during a first patient visit while a second medical image of the two or more medical images may be acquired at a second patient visit. The two patient visits may be spaced apart by a predetermined amount of time. In one scenario, the first patient visit may take place prior to a treatment while the second patient visit may take place after the treatment. In another scenario, the first and second patient visits (and by extension, the two or more medical images of a patient anatomy) may take place during a patient monitoring period during or after a treatment regimen. The embodiments of the present disclosure aim to ascertain whether the two or more temporally-spaced medical images belong to the same patient. In some embodiments, vascular models may be extracted from the received medical images in order to ascertain whether the two or medical images belong to the same patient. For the purposes of the disclosure, "patient" may refer to any individual or person for whom medical images and/or biographical information are being matched, or any individual or person associated with the association or matching of medical images and/or biographical information, or the diagnosis or treatment analysis of one or more individuals.

In one embodiment, step 204 may include receiving patient biographical data (e.g., patient name, date of birth, medical history, information regarding patient gender, weight, height, body mass index, hair color, or eye color, etc.) associated with each of the received medical images in an electronic storage medium. Step 204 may further include determining whether the received patient biographical data associated with each of the received medical images are sufficiently similar. If, for example, the received patient biographical data are not sufficiently similar, steps 202 and 204 may be repeated.

In one embodiment, step 206 may include extracting a vascular, skeletal, muscular, neural, lymphatic, tissue, and/or organ model from each of the received medical images. Specifically, the same corresponding vasculature, bones, muscles, nerves, lymphatic vessels, tissues, and/or organs are extracted from each of the received images. Step 206 may be performed using any standard image segmentation or centerline extraction technique. In one embodiment, step 206 may be performed by a processor of the server systems 106.

Step 208 may include determining a field of view to be used for each of the medical images and/or each of the extracted vascular, skeletal, muscular, neural, lymphatic, tissue and/or organ models, and, optionally, removing any portion of the medical images or models that may be outside the field of view. The new set of medical images and/or models with the same field of view may be saved to an electronic storage medium of the server systems 106.

In one embodiment, steps 210A, 210B, and 210C may include obtaining patient-specific physiological and/or anatomical information regarding each of the received medical images and/or each of the extracted vascular, skeletal, muscular, neural, lymphatic, tissue and/or organ models. The patient-specific physiological and/or anatomical information may be saved into an electronic storage medium of the server systems 106.

For example, step 210A may include determining the physiological and/or biomechanical properties at one or more locations in the vascular, skeletal, muscular, neural, lymphatic, tissue, and/or organ model. For a vascular model, the physiological and/or biomechanical properties may include blood flow characteristics (e.g., blood flow, velocity, pressure, FFR, iFR, axial stress, wall shear stress, strain, force, shape, size, volume, tortuosity, etc.), and may be determined via one or more of, e.g., biophysical simulation, machine learning, and/or association with a database, etc.

In another example, step 210B may include determining pathological properties and/or disease patterns at one or more locations in the vascular, skeletal, muscular, neural, lymphatic, tissue, and/or organ model. The pathological properties and/or disease patterns may include, but are not limited to, location and type of plaque, calcification, rupture risk, necrosis, ischemia, occlusions, tumors, lesions, congenital abnormalities, and/or impact of trauma In another example, step 210C may include determining foreign body properties at one or more locations in the vascular, skeletal, muscular, neural, lymphatic, tissue, and/or organ model. The foreign body properties may include, but are not limited to, the locations and characteristics for an implanted stent, bypass, pacemaker, artificial valve, surgical clip, wire, dental filling, shrapnel, bullet, or an artificial heart and/or donated organ.

In one embodiment, step 212 may include determining a score that assesses the matching between a vascular, skeletal, muscular, neural, lymphatic, tissue, and/or organ model with other vascular, skeletal, muscular, neural, lymphatic, tissue, and/or organ models, respectively ("matching score" or "first matching score"). Alternatively or additionally, the score may be used to assess the matching between the received medical images. The matching score may be calculated in several ways, which are further described in methods 400, 500, and 600 of FIGS. 4, 5, and 6, respectively. For example, calculating a matching score for vascular models may include, but is not limited to, computing a graph matching between one or more graphs representing the two or more vascular networks, performing a point matching of the vessel bifurcations, performing growth and remodeling simulations of vasculature and the vessel walls between time points where the scans where taken, and/or computing an embedding of the received medical images and/or extracted models. Step 212 may be performed by a processor of the server systems 106.

In some embodiments, steps 208, and 210A-C may be optional. In such embodiments, a score may be determined without determining a field of view, for example.

Step 214 may include outputting the matching score to an electronic display and/or an electronic storage device. For purposes of disclosure, an "electronic storage medium" may include, but is not limited to, a hard drive, network drive, cloud drive, mobile phone, tablet, database, or the like that may or may not be affixed to a display screen. In one embodiment, as described in method 300 of FIG. 3, the calculation of the matching score may be further adjusted prior to output by calculating a second score, (e.g., a "second matching score"), the calculation being based on the first matching score as well as a defined metric comparing the similarity of the patient biographical data of the at least two medical images. In another embodiment, medical images and/or models with high matching scores may be used as longitudinal data to evaluate treatment options for a patient.

FIG. 3 is a block diagram of a method 300 for associating medical images to a patient, by extracting a vascular model from each of the received medical images and further adjusting a matching score based on the received patient biographical information, according to an exemplary embodiment. The method of FIG. 3 may be performed by server systems 106, based on information, images, and data received from physicians 102 and/or third party providers 104 over electronic network 101.

In one embodiment, step 302 may include receiving two or more medical images of a patient anatomy in an electronic storage medium of the server systems 106. Specifically, receiving the patient-specific medical images may include either generating the patient-specific medical images at the server system 106, or receiving them over an electronic network (e.g., electronic network 101). The medical images may be derived from images of one or more patients acquired via one or more available imaging or scanning modalities (e.g., computed tomography (CT), magnetic resonance imaging (MRI), single-photon emission computed tomography (SPECT), positron emission tomography (PET), ultrasound imaging, multi-view angiography, etc.). The embodiments of the present disclosure aim to ascertain whether the two or medical images belong to the same patient. In some embodiments, vascular models may be extracted from the received medical images in order to ascertain whether the two or medical images belong to the same patient.

Step 304 may include receiving patient biographical data (e.g., patient name, date of birth, medical history, information regarding patient gender, weight, height, body mass index, hair color, eye color, etc.) associated with each of the received medical images in an electronic storage medium of the server systems 106.

In one embodiment, step 306A may include determining whether the received patient biographical data associated with each of the received medical images are sufficiently similar. Sufficient similarity between the patient biographical data of the received images may be determined by, one or more of, computing the frequency, location, and/or overlap of common letters; computing the frequency, location, and/or overlap of common phonemes; computing the frequency, location, and/or overlap of medical history information; computing the frequency, location, and/or overlap of information regarding patient gender, weight, height, body mass index, hair color, or eye color; using a database of common name typographic errors, switching day and month, day and year or month and year in the birth dates to determine similarity, and/or using numerically similar days, months or years in the birth dates. If, for example, the received patient biographical data are not sufficiently similar, steps 302 and 304 may be repeated. In some embodiments, if the received patient biographical data are not sufficiently similar, step 306B may include indicating that the received medical images may not be matched to the same patient ("no match"). For example, a matching score of '0' may be used to indicate a no match.

If, subsequent to step 306A, there is sufficient similarity between the patient biographical data, then, in one embodiment, step 308 may include extracting a vascular model from each of the received medical images. Specifically, the same corresponding vasculature, is extracted from each of the received images. Step 308 may be performed using any standard image segmentation or centerline extraction technique. In one embodiment, step 308 may be performed by a processor of the server systems 106.

In one embodiment, step 310 may include determining a field of view to be used in each of the medical images and/or the extracted models and, optionally, removing any portion of the medical images or vascular, skeletal, muscular, neural, lymphatic, tissue and/or organ model that may be outside the field of view. The new set of medical images and/or models with the same field of view may be saved to an electronic storage medium of the server systems 106.

In one embodiment, steps 312A, 312B, and 312C may include obtaining patient-specific physiological and/or anatomical information regarding each of the received medical images and/or each of the extracted vascular models. The patient-specific physiological and/or anatomical information may be saved into an electronic storage medium of the server systems 106.

For example, step 312A may include determining the physiological and/or biomechanical properties at one or more locations in the vascular model. For a vascular model, the physiological and/or biomechanical properties may include blood flow characteristics (e.g., blood flow, velocity, pressure, FFR, iFR, axial stress, wall shear stress, strain, force, shape, size, volume, tortuosity, etc.), and may be determined via, one or more of, biophysical simulation, machine learning, association with a database, etc. For example, known vascular anatomical information and known physiological and/or biomechanical properties at one or more locations may be used to train a machine learning algorithm. Then, the trained machine learning algorithm may be used to predict the physiological and/or biomechanical properties at one or more locations of a vascular model with known vascular anatomical information but unknown physiological and/or biomechanical properties.

In another example, step 312B may include determining pathological properties and/or disease patterns at one or more locations in the vascular model. The pathological properties and/or disease patterns may include, but are not limited to, location and type of plaque, calcification, rupture risk, necrosis, ischemia, occlusions, tumors, lesions, congenital abnormalities, and impact of trauma.

In another example, step 312C may include determining foreign body properties at one or more locations in the vascular model. The foreign body properties may include, but are not limited to, the locations and characteristics for an implanted stent, bypass, pacemaker, artificial valve, surgical clip, wire, dental filling, shrapnel, bullet, or an artificial heart and/or organ.

In one embodiment, step 314 may include determining a score that assesses the matching between a vascular model with other vascular models, respectively ("matching score" or "first matching score"). Alternatively or additionally, the score may be used to assess the matching between the received medical images from which the vascular models were extracted. The matching score may be calculated in several ways, which are further described in methods 400, 500, and 600 of FIGS. 4, 5, and 6, respectively. Calculating a matching score for vascular models may include, but is not limited to, computing a graph matching between one or more graphs representing the two or more vascular networks, performing a point matching of the vessel bifurcations, performing growth and remodeling simulations of vasculature and the vessel walls between time points where the images where taken, and/or computing an embedding of the received medical images and/or extracted models. Step 314 may be performed by a processor of the server systems 106. Computing an embedding for a set of feature vectors is a standard technique known to one of ordinary skill in the art. The process may include, e.g., taking a set of feature vectors of length k and recoding the set as a second set of feature vectors of length s, where s<<k. The second feature space, created by the second set, may be more meaningful. For example, the distances between feature vectors in the new space (viewed as points) may represent a more intuitive and/or useful meaning of "close" or "far."

In some embodiments, steps 310, and 312A-C may be optional. In such embodiments, a score may be determined (e.g., as in step 314) without determining a field of view, for example.

In one embodiment, step 316 may include determining a second score (e.g., "second matching score"), the second matching score being based on the first matching score as well as a defined metric comparing the similarity of the patient biographical data of the at least two medical images (e.g., name, date of birth, etc.). Calculating the metric comparing the similarity of patient biographical data may include, but is not limited to, computing the frequency, location, and/or overlap of common letters; computing the frequency, location, and/or overlap of common phonemes; computing the frequency, location, and/or overlap of medical history information; computing the frequency, location, and/or overlap of information regarding patient gender, weight, height, body mass index, hair color, or eye color; using a database of common name typographic errors, switching day and month, day and year or month and year in the birth dates to determine similarity; and using numerically similar days, months or years in the birth dates.

In one embodiment, step 318 may include outputting the matching scores (e.g., first matching score and second matching score) to an electronic display and/or an electronic storage medium of the server systems 106. Those medical images and/or models with high matching scores may be used as longitudinal data to evaluate treatment options for a patient.

FIG. 4 is a block diagram of a method 400 for determining a first matching score between two or more medical images by using graph or point matching, according to an exemplary embodiment. Method 400 of FIG. 4 may be performed by server systems 106, based on information, images, and data received from physicians 102 and/or third party providers 104 over electronic network 101.

In one embodiment, step 402 may include receiving two or more vascular models. Each vascular model may be extracted from a respective received medical image, as described in steps 206 and 308 of methods 200 and 300 in FIGS. 2 and 3, respectively.

In one embodiment, subsequent to step 402, step 404 may include deriving vascular graphs representing the vascular networks from the vascular models. Alternately or additionally, subsequent to step 402, step 404 may include deriving points representing the vessel bifurcations from the vascular models.

Steps 406, 408, 410, and 412 describe the receiving of additional information to be used in graph matching and/or point matching. The additional information may include, but is not limited to, the relationship of the graphs or points to other anatomical models, physiological and/or biomechanical properties, pathological properties, or foreign body properties.

Step 406 may include deriving the relationship of the graphs and/or points obtained in step 404 respectively, to other anatomical models. These other anatomical models may also be extracted from the received medical images and may include, but are not limited to, the skeletal, muscular, neural, lymphatic, tissue, and/or organ models. For example, the relationship may include the distance from each point or node of a graph to one or more locations in the other anatomical models.

Step 408 may include deriving a relationship of the graph and/or points to physiological and/or biomechanical properties at one or more locations of the vascular models. The physiological and/or biomechanical properties may include blood flow characteristics (e.g., blood flow, velocity, pressure, FFR, iFR, axial stress, wall shear stress, strain, force, shape, size, volume, tortuosity, etc.), and may be determined via one or more of, biophysical simulation, machine learning, association with a database, etc.

Step 410 may include deriving a relationship of the graph and/or points to pathological properties or disease patterns for one or more locations of the vascular models. The pathological properties or disease patterns may include, but are not limited to, location and type of plaque, calcification, rupture risk, necrosis, ischemia, occlusions, tumors, lesions, congenital abnormalities, impact of trauma, etc.

Step 412 may include deriving relationship of the graph and/or points to foreign body properties for one or more locations of the vascular model. The foreign body properties may include, but are not limited to, the locations and characteristics for a stent, bypass, pacemaker, artificial valve, surgical clip, wire, dental filling, shrapnel, bullet, or an artificial heart and/or organ. For example, step 412 may include finding the distance from each point or node of a graph to one or more locations of interventional instruments or implanted devices.

In one embodiment, step 414 may include performing graph matching between graphs representing the vascular networks. Performing graph matching may be performed by a processor of the server systems 106, using algorithms and/or techniques including, but not limited to, graph edit distance, spectral matching, diffusion distance, graph motif matching, or a combination thereof. The additional information gained from steps 406, 408, 410, and/or 412 (e.g., relationship of the graphs or points to other anatomical models, physiological and/or biomechanical properties, pathological properties, foreign body properties, etc.) may be treated as feature vectors for the graph matching performed in step 414. The additional information may also be used in a known augmented graph matching algorithm, e.g., FOCUSR.

Alternately or additionally, step 414 may include performing point matching between graphs representing the vascular networks. The point matching may be performed by a processor of the server systems 106, using algorithms and/or techniques, including, but not limited to, iterated closest point matching, robust point matching, thin plate spline robust point matching, kernel correlation, Gaussian mixture models, coherent point drift matching, or a combination thereof. The additional information gained from steps 406, 408, 410, and/or 412 (e.g., relationship of the graphs or points to other anatomical models, physiological and/or biomechanical properties, pathological properties, foreign body properties, etc.) may be treated as feature vectors for the point matching performed in step 414.

Step 416 may include determining a score ("first matching score") that assesses the matching between the two or more medical images. This determination may be based on the performance of the graph matching and/or point matching in step 414. The score may be determined using a processor and may be saved in the electronic storage medium of server systems 106.

FIG. 5 is a block diagram of a method 500 for determining a first matching score between two or more medical images by using growth and remodeling simulations, according to an exemplary embodiment. Method 500 of FIG. 5 may be performed by server systems 106, based on information, images, and data received from physicians 102 and/or third party providers 104 over electronic network 101.

In one embodiment, steps 502A and 502B may include receiving a medical image from an earlier time point and receiving a medical image from a later time point, respectively. The received medical images may be saved to an electronic storage medium of server systems 106. Step 504 may include calculating the time difference between the time points at which the received medical images were obtained.

In one embodiment, steps 506A may include extracting a vascular model from the received medical image of the earlier time point and step 506B may include extracting a vascular model from the received medical image of the later time point. The extraction may be performed using a processor of server systems 106. The extracted vascular models may be saved into the electronic storage medium of the server systems 106.

Steps 508A, 508B, and 508C may include determining additional information regarding the extracted vascular model of the earlier time point, for the purpose of performing a growth and remodeling simulation of the vascular model from the earlier time point. Specifically, step 508A may include determining the physiological and/or biomechanical properties at one or more locations on the vascular model of the earlier time point. The physiological and/or biomechanical properties may include blood flow characteristics (e.g., blood flow, velocity, pressure, FFR, iFR, axial stress, wall shear stress, strain, force, shape, size, volume, tortuosity, etc.), and may be determined via one or more of, e.g., biophysical simulation, machine learning, association with a database, etc. Step 508B may include determining the pathological properties and disease patterns at one or more locations on the vascular model of the earlier time point. The pathological properties or disease patterns may include, but are not limited to, location and type of plaque, calcification, rupture risk, necrosis, ischemia, occlusions, tumors, lesions, congenital abnormalities, impact of trauma, etc. Step 508C may include determining the foreign body properties, if any, at one or more locations of the vascular model of the earlier time point. The foreign body properties may include, but are not limited to, the locations and characteristics for a stent, bypass, pacemaker, artificial valve, surgical clip, wire, dental filling, shrapnel, bullet, or an artificial heart and/or organ.

In some embodiments, steps 508A-C may be optional.

In one embodiment, step 510 may include performing growth and remodeling simulations of the vascular model of the earlier time point over the calculated time difference to predict a vascular model of a later time point. The simulation of the vascular model may include modeling how the radii of the vessels and thickness of the vessel walls may change over the calculated time difference. Such changes may be modeled by solving stress equilibrium equations on the vascular model of the earlier time point, with either population averaged material properties or, if available, patient-specific material properties of the vessel wall(s). Step 510 may be performed using a processor and the simulated vascular model of the later time point may be saved to an electronic storage medium of server systems 106.

In one embodiment, step 512 may include comparing the simulated vascular model of the later time point with the actual vascular model of the later time point from step 506B. Step 512 may include performing a graph matching and/or point matching of the simulated and actual vascular models of the later time point. The graph matching and/or point matching procedure may be performed by, for example, applying method 400 described in FIG. 4.

In one embodiment, step 514 may include determining a score (e.g., a "first matching score") that assesses the matching between the two medical images. This determination may be based on the comparison of the simulated and actual vascular models of the later time point. The score may be determined using a processor and may be saved in the electronic storage medium of server systems 106.

FIG. 6 is a block diagram of a method 600 for determining the first matching score between two or more medical images by computing an embedding of the two or more medical images or a medical image and a graph. Method 600 of FIG. 6 may be performed by server systems 106, based on information, images, and data received from physicians 102 and/or third party providers 104 over electronic network 101.

In one embodiment, step 602 may include receiving two or more medical images in an electronic storage medium. Receiving the patient-specific medical images may include either generating the patient-specific medical images at the server system 106, or receiving them over an electronic network (e.g., electronic network 101). The medical images may be derived via one or more available imaging or scanning modalities (e.g., computed tomography (CT), magnetic resonance imaging (MRI), single-photon emission computed tomography (SPECT), positron emission tomography (PET), ultrasound imaging, multi-view angiography, etc.).

Step 604 may include receiving any patient-specific biographical information associated with the received two or more medical images. The biographical information may include, but is not limited to, patient age, date of birth, medical history, and information regarding patient gender, weight, height, body mass index, hair color, or eye color.

Steps 606, 608, and 610A-D may enable the embedding of a medical image and a graph. In one embodiment, step 606 may include extracting one or more vascular models from each medical image received in step 602. Each vascular model may be extracted as described in steps 206 and/or 308 of methods 200 and 300 in FIGS. 2 and 3, respectively. Step 606 may include deriving graphs representing the vascular networks from the extracted vascular models. In various embodiments, a graph may refer to a collection of points (or nodes) connected by links. The points may be distributed along the vessel centerlines, with links connecting neighboring points.

Steps 610A-D may describe the receiving of additional information to be used for embedding a medical image with a graph. The additional information may include, but is not limited to, the relationship of the graphs to other anatomical models, physiological and/or biomechanical properties, pathological properties, or foreign body properties.

Step 610A may include deriving the relationship of the graph obtained in step 608 to other anatomical models. These other anatomical models may also be extracted from the received medical image and may include, but are not limited to, the skeletal, muscular, neural, lymphatic, tissue, and/or organ model. For example, the relationship may include the distance from each node of a graph to one or more locations in the other anatomical models.

Step 610B may include deriving the relationship of the graph obtained in step 608 to other physiological and/or biomechanical properties at one or more locations of the vascular models. The physiological and/or biomechanical properties may include blood flow characteristics (e.g., blood flow, velocity, pressure, FFR, iFR, axial stress, wall shear stress, strain, force, shape, size, volume, tortuosity, etc.), and may be determined via one or more of, e.g., biophysical simulation, machine learning, association with a database, etc.

Step 610C may include deriving the relationship of the graph obtained in step 608 to pathological properties or disease patterns for one or more locations of the vascular models. The pathological properties or disease patterns may include, but are not limited to, location and type of plaque, calcification, rupture risk, necrosis, ischemia, occlusions, tumors, lesions, congenital abnormalities, impact of trauma, etc.

Step 610D may include deriving the relationship of the graph to foreign body properties for one or more locations of the vascular model. The foreign body properties may include, but are not limited to, the locations and characteristics of a stent, bypass, pacemaker, artificial valve, surgical clip, wire, dental filling, shrapnel, bullet, or an artificial heart and/or organ. For example, step 610D may include finding the distance from each node of a graph to one or more locations of interventional instruments or implanted devices.

In one embodiment, the additional information used for embedding a medical image with a graph may also include patient-specific biographical information associated with one or more medical images.

Step 612 may include computing an embedding of the two or more medical images or a medical image and a graph using any additionally received information from steps 604 or 610A-D. The embedding may be calculated generally, by using isomap, local linear embedding or any other linear or non-linear dimensionality reduction technique, or specifically, by using convolutional, feed-forward or recurrent neural networks. The embedding may potentially be trained using a twin or Siamese network. Step 612 may be performed by a processor and the results of the embedding may be stored in an electronic storage medium of server systems 106.

Step 614 may include comparing the similarity of the medical images or a medical image and a graph in the embedding space. In one embodiment, the embedding may incorporate additional information regarding the medical images and/or graph, including, but not limited to, patient-specific biographical information, relationships of a graph to other anatomical models, physiological and/or biomechanical properties, pathological properties, and/or foreign body properties. In one embodiment, the similarity may be compared using feed-forward or recurrent neural networks.

Step 616 may include determining a score (e.g., a "first matching score") that assesses the matching between the two or more medical images. The score may be based on the comparing the similarity of the medical images or a medical image and a graph in the embedding space. Steps 614 and 616 may be performed using a processor and the results may be saved in an electronic storage medium of server systems 106.

FIG. 7 is a block diagram of a method 700 for matching at least two medical images to a patient using a first matching score and patient biographical data. Method 700 of FIG. 7 may be performed by server systems 106, based on information, images, and data received from physicians 102 and/or third party providers 104 over electronic network 101.

In one embodiment, step 702 may include receiving at least two medical images in an electronic storage medium. The medical images may be the same as the medical images used to determine a first and/or second matching score, as described in methods 200, 300, 400, 500, and 600 of FIGS. 2, 3, 4, 5, and 6, respectively.

In one embodiment, step 704 may include receiving patient biographical data associated with the medical images in an electronic storage medium. The received patient biographical data may be the same as the patient biographical data that have been used to determine a first and/or second matching score, as described in methods 200, 300, 400, 500, and 600 of FIGS. 2, 3, 4, 5, and 6, respectively.

In one embodiment, step 706 may include receiving a first matching score that assesses the matching between the two or more medical images. The first matching score may be determined, for example, by computing a graph matching between one or more graphs representing the two or more vascular networks, performing a point matching of the vessel bifurcations (e.g., as in FIG. 4), performing growth and remodeling simulations of vasculature and the vessel walls between time points where the scans where taken (e.g., as in FIG. 5), and/or computing an embedding of the received medical images and/or extracted models (e.g., as in FIG. 6).

In one embodiment, subsequent to step 706, step 708 may include determining whether the first matching score is sufficiently high, e.g., above a predetermined threshold. If the first matching score is not sufficiently high, steps 702, 704, and 706 may be repeated using a new set of at least two medical images. In some embodiments, if the first matching score is not sufficiently high, step 712B may include indicating that the received medical images may not be matched to the same patient ("no match"). For example, a first matching score of '0' may be used to indicate a no match.

If the first matching score is sufficiently high, then step 710 may include determining whether the received patient biographical data are sufficiently similar, e.g., similar beyond a predetermined threshold of similarities. In one embodiment, the patient biographical data may only be compared for sufficient similarity if the medical images, with which the patient biographical data are associated with, have a high first matching score. In one embodiment, patient biographical data would be determined to not be sufficiently similar if it is more likely than not that the patient biographical data pertain to different patients. In one embodiment, sufficient similarity between patient biographical data may be determined by computing the frequency, location, and/or overlap of common letters; computing the frequency, location, and/or overlap of common phonemes; computing the frequency, location, and/or overlap of medical history information; computing the frequency, location, and/or overlap of information regarding patient gender, weight, height, body mass index, hair color, or eye color; and using a database of common name typographic errors, switching day and month, day and year or month and year in the birth dates to determine similarity, using numerically similar days, months or years in the birth dates, or a combination thereof.

If, subsequent to step 710, the patient biographical data is determined to be sufficiently similar, then in one embodiment, step 712A may include matching the patient associated with the sufficiently similar patient biographical data to the medical images.

If, subsequent to step 710, the second matching score is not sufficiently high, step 712B may include indicating that the received medical images may not be matched to the same patient ("no match). For example, a second matching score of '0' may be used to indicate a no match.

In one embodiment, method 700 may be performed by a processor of server systems 106, and the result of the matching may be stored in an electronic storage medium of server system 106 or displayed.

Alternatively, or in addition to using the vascular model as the primary model for matching and determining the first and/or second matching score in methods 300, 400, 500, or 600, a skeletal, muscular, neural, lymphatic, tissue, and/or organ model may similarly be used. For example, the graph matching in method 400 may include using a pattern (e.g., network, topology, etc.) of a skeletal, muscular, organ, neural, lymphatic, tissue, and or organ model as an alternative or in addition to using the vascular network of a vascular model. The shape, location, and/or pathology of elements (e.g., papillary muscles) of a skeletal, muscular, neural, lymphatic, tissue, and/or organ model may also be used for matching and/or determining a first and/or second matching score.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of associating medical images with a patient, the method comprising:
    receiving, in an electronic storage medium, a first medical image of first patient anatomy at a first time and a second medical image of second patient anatomy at a second time, the second time being subsequent to the first time;
    generating a first anatomical model for the received first medical image by simulating a change in the first patient anatomy from the first time to the second time, the first anatomical model being a simulated model, obtained by the simulating, that represents a prediction of the first patient anatomy at the second time;
    generating a second anatomical model for the received second medical image, the second anatomical model representing the second patient anatomy at the second time;
    comparing the generated first and second anatomical models;
    determining a score assessing the likelihood that the first and second medical images belong to the same patient, using a comparison result of the comparing the generated first and second anatomical models; and
    outputting the score to an electronic storage medium or display.

2. The computer-implemented method of claim 1, further comprising:
    receiving patient biographical information associated with the received first and second medical images in an electronic storage medium;
    comparing the patient biographical information for the first and second medical images;
    determining whether the patient biographical information for the first and second medical images provide sufficient identifying information for a possible patient, the sufficiency of the identifying information based on a predetermined threshold;
    matching the received first and second medical images to a possible patient, if there is a high score assessing the likelihood that the first and second medical images belong to the same patient, and if there is sufficient identifying information for a possible patient; and
    outputting the identifying information of the possible patient that has been matched to the first and second medical images, to an electronic storage medium or display.

3. The computer-implemented method of claim 1, further comprising:
    defining a field of view for each of the first and second anatomical models,
    wherein the comparing the generated first and second anatomical models is based on the defined field of view.

4. The computer-implemented method of claim 1, wherein each of the generated first and second anatomical models includes one or more of:
    a vascular anatomical model;
    a skeletal anatomical model;
    a muscular anatomical model;
    a neural anatomical model;
    a lymphatic anatomical model;
    an anatomical model of a tissue; or
    an anatomical model of an organ.

5. The computer-implemented method of claim 1, wherein the comparing the generated first and second anatomical models includes using available patient-specific information to compare the first and second anatomical models, the patient-specific information including, one or more of:
    a relationship of one type of anatomical model generated from a medical image to another type of anatomical model generated from the same medical image;

a physiological or biomechanical property of an anatomical model;
a pathological property or disease pattern of an anatomical model; and
a foreign body property of an anatomical model.

6. The computer-implemented method of claim 1, wherein the comparing the generated first and second anatomical models includes:
embedding (1) the received first and second medical images, (2) the generated first and second anatomical models, or (3) patient biographical information respectively associated with the received first and second medical images, in an embedding space; and
comparing (1) the received first and second medical images, (2) the generated first and second anatomical models, or (3) the patient biographical information respectively associated with the received first and second medical images, in the embedding space.

7. The computer-implemented method of claim 1, wherein the comparing the generated first and second anatomical models includes:
deriving a graph representing networks within the generated anatomical model generated for one among the first and second medical images, or points representing bifurcations of the networks;
deriving relationships of the derived graph or points to, one or more of, another type of anatomical model generated from the first and second medical images, a physiological or biomechanical property of the first and second anatomical models, a pathological property or disease pattern of the first and second anatomical models, or a foreign body property of the first and second anatomical models;
embedding the graph in an embedding space using the derived relationships;
embedding, in an embedding space, another among the first and second medical images; and
comparing the graph and the another among the first and second medical images in the embedding space.

8. The computer-implemented method of claim 1, wherein the comparing the generated first and second anatomical models includes:
deriving graphs representing networks within the generated first and second anatomical models;
deriving relationships of the derived graphs to, one or more of, another type of anatomical model generated from the first and second medical images, a physiological or biomechanical property of the first and second anatomical models, a pathological property or disease pattern of the first and second anatomical models, or a foreign body property of the first and second anatomical models; and
performing a graph matching between graphs representing the networks using the derived relationships.

9. The computer-implemented method of claim 1, wherein the comparing the generated first and second anatomical models includes:
deriving points representing bifurcations of networks within the generated first and second anatomical models;
deriving relationships of the derived points to at least one of another type of anatomical model generated from the first and second medical images, a physiological or biomechanical property of the first and second anatomical models, a pathological property or disease pattern of the first and second anatomical models, or a foreign body property of the first and second anatomical models; and
performing a point matching between the points representing bifurcations of networks using the derived relationships.

10. The computer-implemented method of claim 1, wherein the generating the first anatomical model includes:
generating an anatomical model from the first medical image;
performing a growth and remodeling simulation on the anatomical model generated from the first medical image to predict the first anatomical model, using a difference in time between the first and second times and using one or more patient-specific information, the patient-specific information including, one or more of,
a physiological or biomechanical property,
a pathological property or a disease pattern, or
a foreign body property.

11. A system for associating medical images to a patient, the system comprising:
a data storage device storing instructions for associating medical images to a patient; and
a processor configured to execute the instructions to perform a method including:
receiving, in an electronic storage medium, a first medical image of first patient anatomy at a first time and a second medical image of second patient anatomy at a second time, the second time being subsequent to the first time;
generating a first anatomical model for the received first medical image by simulating a change in the first patient anatomy from the first time to the second time, the first anatomical model being a simulated model, obtained by the simulating, that represents a prediction of the first patient anatomy at the second time;
generating a second anatomical model for the received second medical image, the second anatomical model representing the second patient anatomy at the second time;
comparing the generated first and second anatomical models;
determining a score assessing the likelihood that the first and second medical images belong to the same patient, using a comparison result of the comparing the generated first and second anatomical models; and
outputting the score to an electronic storage medium or display.

12. The system of claim 11, wherein the method further comprises:
receiving patient biographical information associated with the received first and second medical images in an electronic storage medium;
comparing the patient biographical information for the first and second medical images;
determining whether the patient biographical information for the first and second medical images provide sufficient identifying information for a possible patient, the sufficiency of the identifying information based on a predetermined threshold;
matching the received first and second medical images to a possible patient, if there is a high score assessing the likelihood that the first and second medical images belong to the same patient, and if there is sufficient identifying information for a possible patient; and outputting the identifying information of the possible patient that has been matched to the two or more medical images, to an electronic storage medium or display.

13. The system of claim 11, wherein
the method further comprises defining a field of view for each of the first and second anatomical models, and
the comparing the generated first and second models is based on the defined field of view.

14. The system of claim 11, wherein the comparing the generated first and second anatomical models includes using available patient-specific information to compare the first and second anatomical models, the patient-specific information including, one or more of:
a relationship of one type of anatomical model generated from a medical image to another type of anatomical model generated from the same medical image;
a physiological or biomechanical property of an anatomical model;
a pathological property or disease pattern of an anatomical model; and
a foreign body property of an anatomical model.

15. The system of claim 11, wherein the comparing the generated first and second anatomical models includes:
embedding (1) the received first and second medical images, (2) the generated first and second anatomical models, or (3) patient biographical information respectively associated with the received first and second medical images, in an embedding space; and
comparing (1) the received first and second medical images, (2) the generated first and second anatomical models, or (3) the patient biographical information respectively associated with the received first and second medical images, in the embedding space.

16. The system of claim 11, wherein the comparing the generated first and second anatomical models includes:
deriving a graph representing networks within the generated anatomical model generated for one among the first and second medical images, or points representing bifurcations of the networks;
deriving relationships of the derived graph or points to, one or more of, another type of anatomical model generated from the first and second medical images, a physiological or biomechanical property of the first and second anatomical models, a pathological property or disease pattern of the first and second anatomical models, or a foreign body property of the first and second anatomical models;
embedding the graph in an embedding space using the derived relationships;
embedding, in an embedding space, another among the first and second medical images; and
comparing the graph and the another among the first and second medical images in the embedding space.

17. The system of claim 11, wherein the comparing the generated first and second anatomical models includes one or more of:
deriving graphs representing networks within the generated first and second anatomical models;
deriving relationships of the derived graphs to, one or more of, another type of anatomical model generated from the first and second medical images, a physiological or biomechanical property of the first and second anatomical models, a pathological property or disease pattern of the first and second anatomical models, or a foreign body property of the first and second anatomical models; and
performing a graph matching between graphs representing the networks using the derived relationships.

18. The system of claim 11, wherein the generating the first anatomical model includes:
generating an anatomical model from the first medical image;
performing a growth and remodeling simulation on the anatomical model generated from the first medical image to predict the first anatomical model, using a difference in time between the first and second times and using one or more patient-specific information, the patient-specific information including, one or more of,
a physiological or biomechanical property,
a pathological property or a disease pattern, or
a foreign body property.

19. A non-transitory computer-readable medium storing instructions that, when executed by a computer, cause the computer to perform a method for associating medical images with a patient, the method including:
receiving, in an electronic storage medium, a first medical image of first patient anatomy at a first time and a second medical image of second patient anatomy at a second time, the second time being subsequent to the first time;
generating a first anatomical model for the received first medical image by simulating a change in the first patient anatomy from the first time to the second time, the first anatomical model being a simulated model, obtained by the simulating, that represents a prediction of the first patient anatomy at the second time;
generating a second anatomical model for the received second medical image, the second anatomical model representing the second patient anatomy at the second time;
comparing the generated first and second anatomical models;
determining a score assessing the likelihood that the first and second medical images belong to the same patient, using a comparison result of the comparing the generated first and second anatomical models; and
outputting the score to an electronic storage medium or display.

20. The non-transitory computer-readable medium of claim 19, wherein the generating the first anatomical model includes:
generating an anatomical model from the first medical image;
performing a growth and remodeling simulation on the anatomical model generated from the first medical image to predict the first anatomical model, using a difference in time between the first and second times and using one or more patient-specific information, the patient-specific information including, one or more of,
a physiological or biomechanical property,
a pathological property or a disease pattern, or
a foreign body property.

* * * * *